United States Patent
Austin

[19]

[11] Patent Number: 6,043,742

[45] Date of Patent: Mar. 28, 2000

[54] APPARATUS AND PROCESS FOR DETECTING MAN-MADE GEMSTONES

[76] Inventor: James Austin, 27049 Rio Bosque, Valencia, Calif. 91354

[21] Appl. No.: 09/303,946

[22] Filed: May 6, 1999

Related U.S. Application Data

[60] Provisional application No. 60/083,467, Apr. 29, 1998.
[51] Int. Cl.⁷ .................................................. G08B 21/00
[52] U.S. Cl. .................. 340/540; 364/560; 364/715; 356/30; 356/301; 356/432; 250/461.1
[58] Field of Search ............................ 340/540; 364/560, 364/715; 356/30, 301, 432; 250/461.1

[56] References Cited

U.S. PATENT DOCUMENTS

| | | | |
|---|---|---|---|
| 4,394,580 | 7/1983 | Gielisse | 250/461.1 |
| 4,845,646 | 7/1989 | Marquis et al. | 364/560 |
| 5,351,117 | 9/1994 | Stewart et al. | 356/30 |
| 5,835,205 | 11/1998 | Hunter et al. | 356/30 |

*Primary Examiner*—Jeffery A. Hofsass
*Assistant Examiner*—Tai T. Nguyen
*Attorney, Agent, or Firm*—Kelly Bauersfeld Lowry & Kelley, LLP

[57] ABSTRACT

An apparatus and process for detecting man-made gemstones using an alternating current conducted through a sample gemstone is provided. The apparatus includes a hand-held housing in which is disposed electronic circuitry, a probe which extends from the housing, and a transmitting stimulus electrode in the form of a body-contact touchpad. The electronic circuitry includes a filter for eliminating non-transmitted signals sensed by the probe, and produces an alternating current signal, preferably in sine wave form, for delivery to the touchpad. The alternating current signal is transmitted through the operator of the apparatus into the sample gemstone. The operator probes the gemstone by touching the conductive probe to the gemstone in an attempt to sense signals conducted through the gemstone. An alarm is activated upon the detection of the conducted transmitted signal, indicating that the gemstone is man-made.

20 Claims, 5 Drawing Sheets

APPARATUS AND PROCESS FOR DETECTING MAN-MADE GEMSTONES

RELATED APPLICATION

This application is a continuation of the utility application filed Apr. 29, 1999 which claimed priority from provisional application Ser. No. 60/083,467 filed Apr. 29, 1998.

BACKGROUND OF THE INVENTION

This present invention relates to the diamond and jewelry industry and is directed to the need for a means of easily and rapidly identifying man-made gemstone simulants.

Many types of simulated diamonds have been created and are cut to resemble diamond for many reasons. The most common of these simulants have been cubic zirconia, synthetic colorless sapphire, yttrium aluminum garnet (YAG), gadolinium gallium garnet (GGG), synthetic spinel, synthetic rutile and strontium titanate. Although most are for legitimate use in low priced jewelry applications, unfortunately, some are used for fraudulent purposes.

Although most of these simulants are readily detected by persons who have been trained to recognize physical properties such as the refractive index, dispersion of light, hardness and other qualities of the gemstone which differentiate these materials from genuine natural diamond, lay people are easily fooled by these simulants. Until recently, one of the most effective means of detecting simulants was to use a device which could measure the relative thermal conductivity of the simulant materials and compare this property to that of natural diamond. These devices depend upon the fact that diamond conducts heat more rapidly than any of the above materials being cut to resemble diamond.

However, there are other simulants which conduct heat in a similar manner as natural diamond. One of these simulant materials is colorless or near-colorless synthetic diamond grown with the preferred nickel catalyst method. A more recently developed diamond simulant is synthetic moissanite (silicon carbide) which has very similar physical properties as natural diamond. A thermal testing of synthetic moissanite or colorless synthetic diamond will test positive as natural diamond. Additionally, although there are differences in hardness, specific gravity, refractive index and dispersion between natural diamond and moissanite, due to the oftentimes only slight differences in these physical properties even trained professionals have difficulty distinguishing between the two.

Research into the properties of silicon carbide (moissanite) revealed that it was being used in semiconductor applications which led to the conclusion that differences in resistivity and/or electrical conductance could be detected in the silicon carbide material which could be used as a distinguishing characteristic between natural diamond, with the exception of a very rare type IIB blue diamond, and synthetic moissanite. Accordingly, devices have been produced which attempt to measure the conductivity of synthetic moissanite samples. Testing of moissanite samples further revealed that although silicon carbide was conductive in many cases, there are also samples which are only semi-conductive. Furthermore, the various facets of the moissanite gemstone and the semi-conductive portions of the gemstone create a diodic junction which allows direct current only through certain connecting points of the gemstone. Prior detection devices have utilized high voltage direct current (DC) signals in an attempt to stimulate and detect conductivity by exceeding the reverse breakdown voltage of these junctions. Due to the power requirements, these devices are commonly plugged into an external power source such as a wall outlet. Even with the increased voltage levels, prior moissanite detecting devices must thoroughly probe the gemstone to find conductive connecting points. These points can be quite difficult to find in semi-conductive gemstones, and if not found the tester falsely determines the moissanite sample to be natural diamond.

It has been observed through experimentation that certain man-made gemstones, such as moissanite, exhibit diode-like characteristics when tested with metal probes, and that those characteristics vary in both degree and polarity from sample to sample. It is therefore desirable to employ an alternating current through the gemstone sample to maximize the likelihood of detecting conductive points on such samples.

Therefore, what is needed is a detector for man-made gemstones which can be used to detect synthetic gemstones which cannot be detected by heat conductivity devices. What is also needed is a detector which is unaffected by the diodic effect of man-made gemstones and is able to detect conductivity in conductive and semi-conductive gemstones. Further, a detector is needed which is small, uncomplicated and battery powered. The present invention fulfills these needs and provides other related advantages.

SUMMARY OF THE INVENTION

The present invention resides in an apparatus and process for differentiating natural diamond from man-made gemstones using an alternating current conducted through a sample gemstone. The apparatus comprises, generally, an electrode which delivers an alternating current stimulus generated by electronic circuitry, and a probe conductively coupled to sensing electronic circuitry.

In its preferred form, the apparatus comprises a hand-held housing in which is disposed the electronic circuitry and from which extends the probe and the transmitting stimulus electrode in the form of a body-contact touchpad. A power source, preferably in the form of a battery disposed within the housing, provides power for the electronic circuitry. The electronic circuitry includes a filter comprised of a transimpedance amplifier and a synchronous detector comprised of an inverting/non-inverting amplifier and a low-pass filter for eliminating non-transmitted signals sensed by the probe. The electronic circuitry also includes means for producing an alternating current sine wave stimulus signal. Upon detection of the transmitted signal, an audible or light-emitting diode alarm indicates to the user the presence of a man-made gemstone.

In order to test a sample gemstone, an operator of the apparatus powers on the apparatus and holds the housing with at least a portion of the operator's body contacting the touchpad while holding the gemstone in the other hand and probes the gemstone by touching the probe of the apparatus to the surface of the gemstone. The electronic circuitry produces an alternating current signal in sine wave form and delivers this signal to the touchpad. A detector switching signal in phase with the alternating current signal as well as a direct current bias voltage are also created by the circuitry. The alternating current signal is transmitted through the operator of the apparatus touching the touchpad and into the sample gemstone.

The operator probes the gemstone by touching the conductive probe to the gemstone in an attempt to sense signals conducted through the gemstone. When a signal is sensed by the probe, the electronic circuitry utilizes a filter to determine whether the sensed signal is the transmitted signal or a non-transmitted signal, such as noise or capacitively coupled signals. Detecting and filtering the signal is accomplished by chopping a portion of any ninety degree shifted, capacitively coupled sensed signal, comparing the phase of the sensed signal with the detector switching signal, rectifying the signal into a direct current, and measuring an increase in voltage over the bias voltage which has been superimposed on the sensed signal. When the circuitry determines that the transmitted signal has been conducted through the gemstone, an alarm is activated to notify the user that the sample gemstone has conducted the transmitted signal and that the sample gemstone is not diamond.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENT

Figure 1:
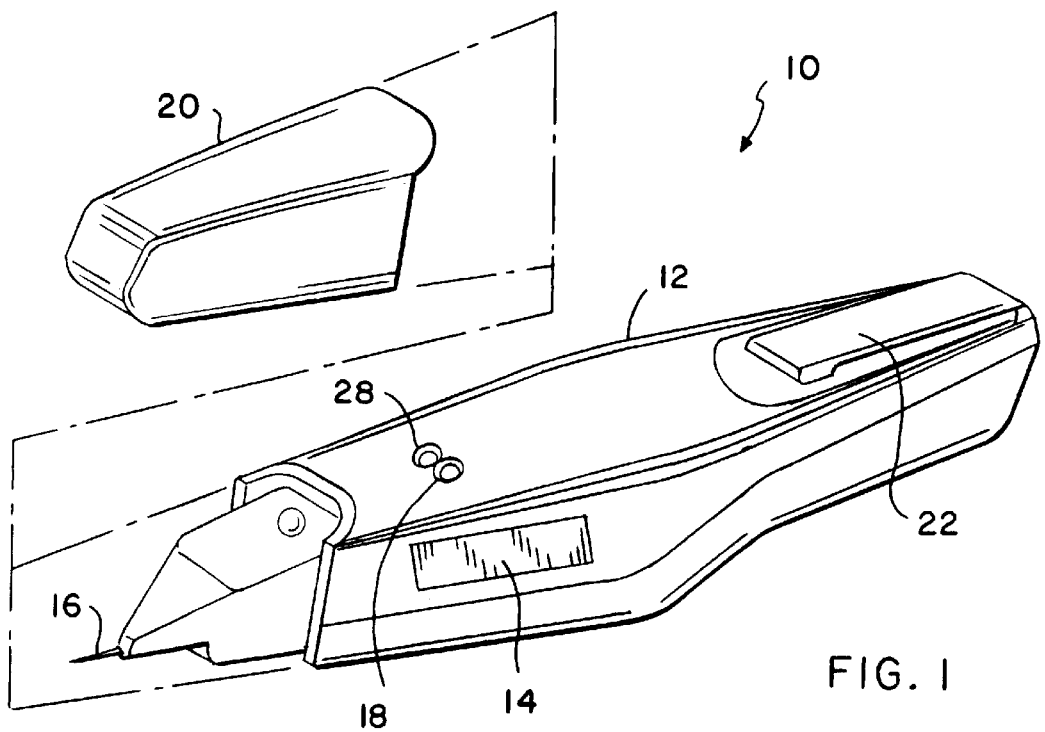
FIG. 1 is a partially exploded perspective view of a detecting apparatus of the present invention, illustrating a protective cap removed from an end of the housing to reveal a conductive probe.
Figure 2:
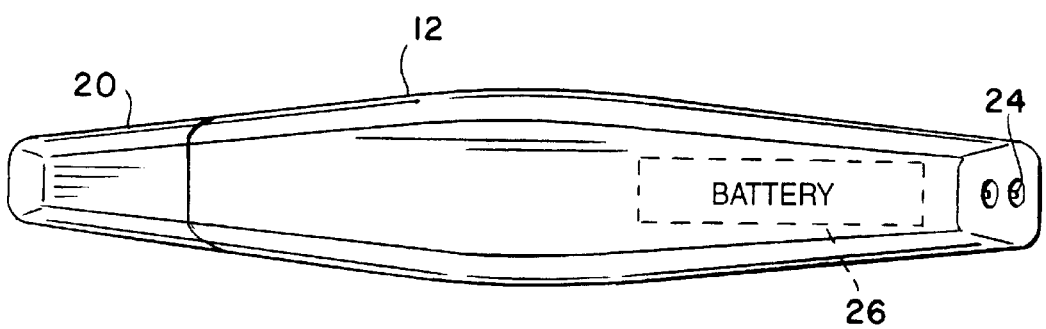
FIG. 2 is a bottom planar view of the apparatus of FIG. 1, illustrating a battery (in phantom) disposed within the housing.
Figure 3:
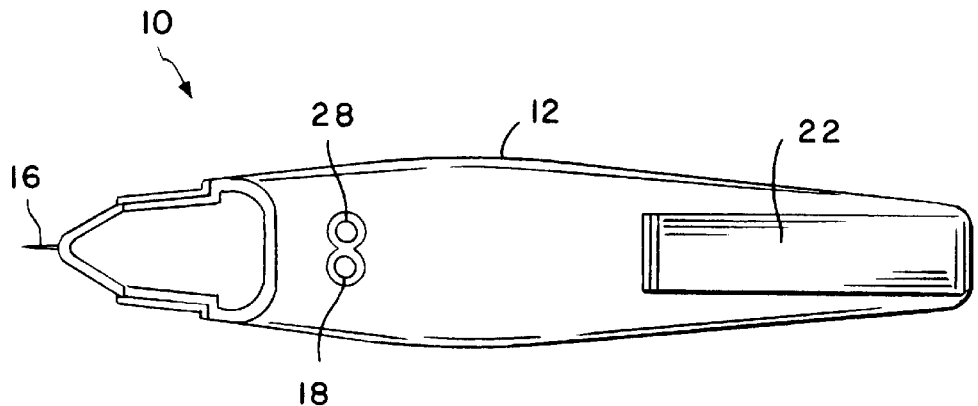
FIG. 3 is a top planar view of the apparatus of FIG. 1.

In accordance with the invention, a detecting apparatus, generally referred to by the reference number 10, is provided for distinguishing between natural diamonds and man-made simulants, including moissanite. The apparatus 10 comprises a hand-held housing 12 in which is disposed electronic circuitry, a signal transmitting stimulus electrode in the form of a body-contact touchpad 14 extending through or on the surface of the housing 12, a conductive probe 16, and an alarm 18 (FIGS. 1–3).

The conductive probe 16 is typically formed of a rigid conductive metal and may be coated with gold or other highly conductive metals to enhance its signal sensing abilities. The apparatus may be constructed such that the probe 16 is attached to a spring (not shown) which allows the probe 16 to partially retract into the housing 12 upon contact with a rigid surface so as to protect the metal probe 16 from being bent or broken while in use. The apparatus may also include a cap 20, as illustrated in FIG. 1, which removably attaches to the housing 12 and covers the probe 16, acting to protect the probe 16 when the apparatus is not in use.

The stimulus electrode touchpad 14 is formed of any suitable conductive material which is comfortable to the operator's touch, such as small copper wires or a metal plate resting on the surface of the housing 12. The touchpad 14 is preferably located on either side of the housing 12 and is of such size that the operator of the apparatus 10 can easily grip it while in body contact with the touchpad 14.

The alarm 18 may be any suitable audible or visual alarming device, but is preferably a red light-emitting diode. The housing 12 may also include a pocket-clip 22 for holding the apparatus 10 in the operator's pocket for easy retrieval. Although the apparatus 10 may be powered by an external source such as a wall socket through a plug 24 in the housing 12, the apparatus 10 can also be powered by a battery 26 disposed within the housing, as illustrated in FIG. 3, to allow the operator to freely transport the apparatus 10 without the concern for external power. The battery 26 is disposed within a battery compartment within the housing 12, and is normally enclosed by a cover 27.

Figure 4:
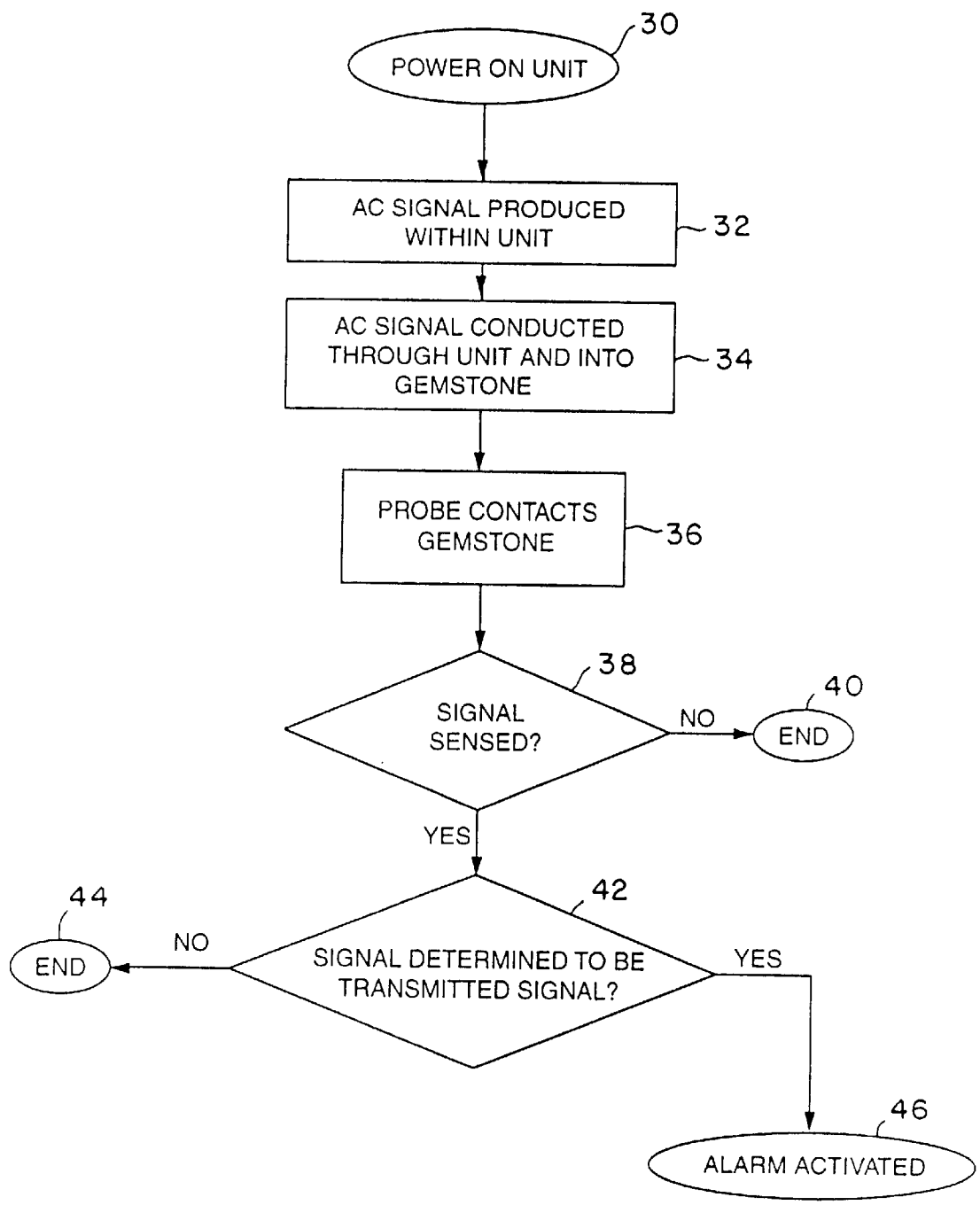
FIG. 4 is a flowchart generally depicting a process for detecting man-made gemstones, in accordance with the present invention.
Figure 5:
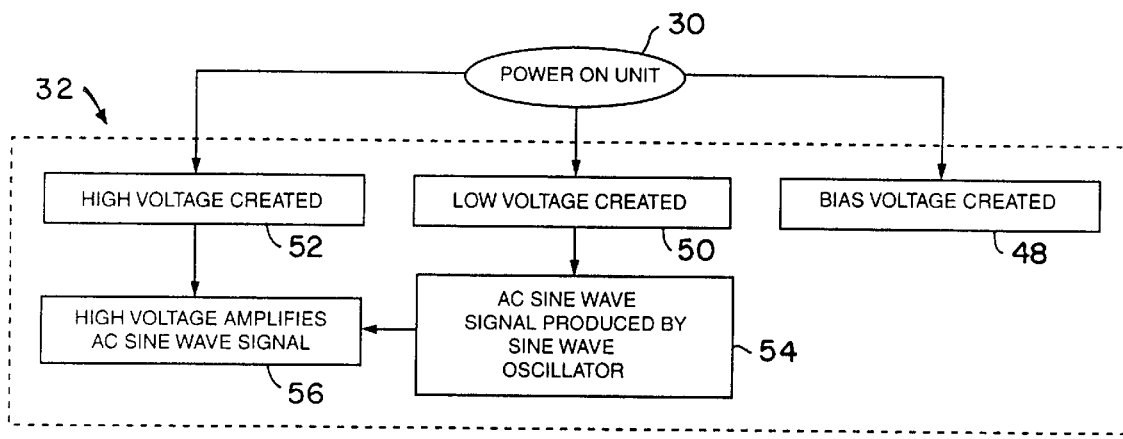
FIG. 5 is a flowchart which elaborates on the step of producing an AC signal, shown in FIG. 4.
Figure 6:
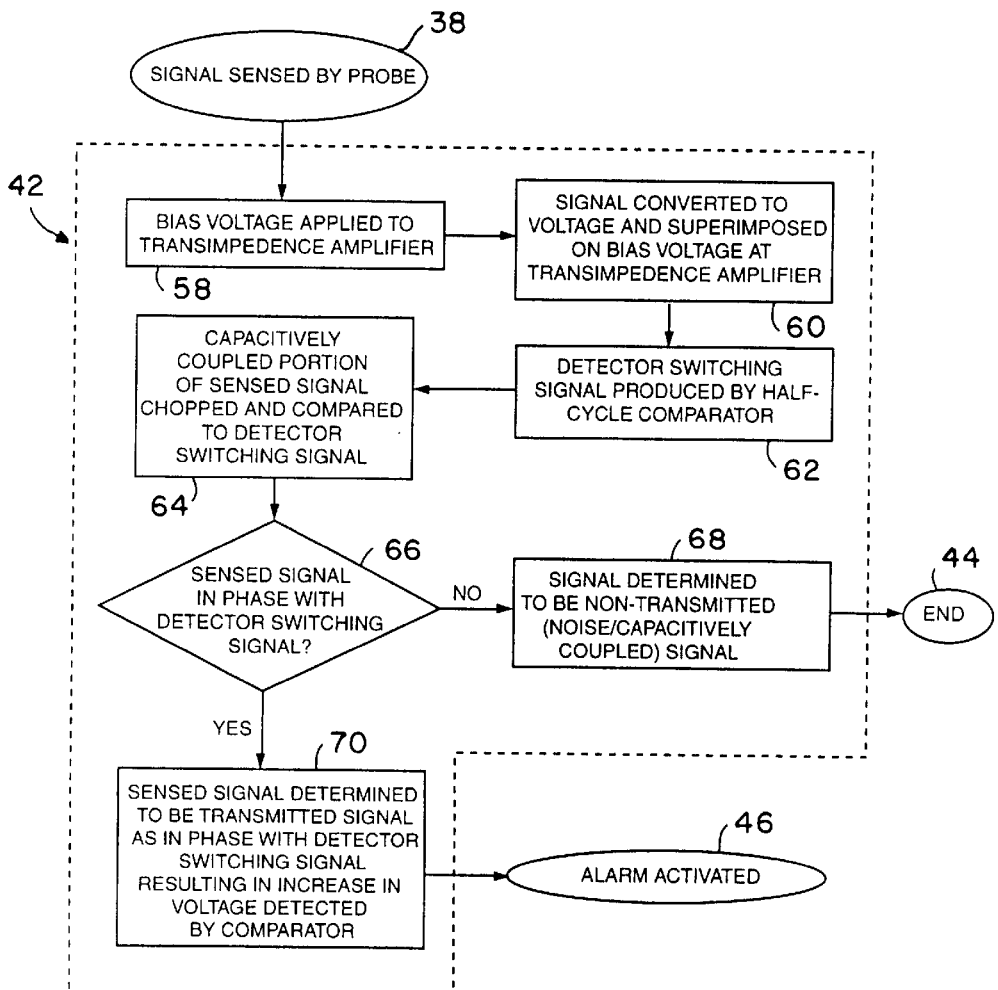
FIG. 6 is a flowchart which elaborates on the step of determing whether the sensed signal is the transmitted signal, shown in FIG. 4.

The process illustrated in FIGS. 4–6 are followed when a sample gemstone is to be tested. Preferably a green light-emitting diode 28 is lit when the apparatus 10 is powered on (block 30) to indicate that the apparatus 10 has sufficient power. An alternating current is produced within the apparatus (block 32), and is conducted through the apparatus 10 and into the sample gemstone (block 34). The probe 16 is brought into contact with the gemstone (block 36) in an attempt to sense a signal (block 38). If no signal is sensed after probing the gemstone, the alarm is not activated and the operator knows that the gemstone is diamond, thus ending the process at block 40. However, if a signal is sensed, the electronic circuitry determines whether the sensed signal is the signal transmitted from the apparatus (block 42). If the signal is not the transmitted signal, nothing happens and the operator knows that the sample gemstone is most likely diamond as it is not conductive, and the process is ended at block 44. If the signal is determined to be the transmitted signal, the alarm is activated at block 46.

FIG. 5, elaborates on the step of producing an AC signal as shown in block 32 of FIG. 4. After powering on the apparatus 10, a bias voltage is created (block 48), a low voltage is created (block 50), and a high voltage is created (block 52). A sine wave oscillator converts the low voltage into an alternating current sine wave signal (block 54) which is amplified by the high voltage amplifier (block 56).

Referring to FIG. 6, once a signal is sensed the following steps occur to determine whether the signal is the transmitted signal (block 42). The bias voltage is constantly applied to a transimpedance amplifier of the electronic circuitry (block 58). The sensed signal is converted to voltage and superimposed on the bias voltage at the transimpedance amplifier (block 60). A detector switching signal having an alternating current, typically in square wave, in phase with the transmitted signal is produced by a half-cycle comparator (block 62). It is a characteristic of capacitance that in the presence of an alternating current stimulus, the current through the capacitance leads the voltage across it in phase by ninety degrees, resulting in the sensing circuitry sensing non-transmitted signals such as harmonic noise and other capacitively coupled signals. Therefore, some stimulus will be coupled capacitively to the sensing probe due to the close proximity of the stimulus electrode and the probe. Thus, the circuit must differentiate between capacitively coupled signals and the transmitted signal conducted through the sample. To achieve this, a synchronous detection method is employed which is responsive to in-phase signals, while rejecting signals exhibiting the leading phase characteristic of capacitive coupling. Therefore, a capacitively coupled portion of the sensed signal is chopped off and the signal is compared to the detector switching signal (block 64) to determine whether or not the sensed signal is in phase with the detector switching signal (block 66). If the sensed signal is not in phase with the detector switching signal, the signal is determined to be noise or other capacitively coupled, non-transmitted signals 68 and nothing happens resulting in the end of the process (block 44) and the determination that the gemstone is most likely diamond as it is not conductive. However, if the sensed signal is determined to be the transmitted signal as it is in phase with the detector switching signal, the result is an increase in voltage detected by a comparator (block 70) which activates the alarm (block 46) indicating to the operator of the apparatus 10 that the gemstone is a man-made simulant.

Figure 7:
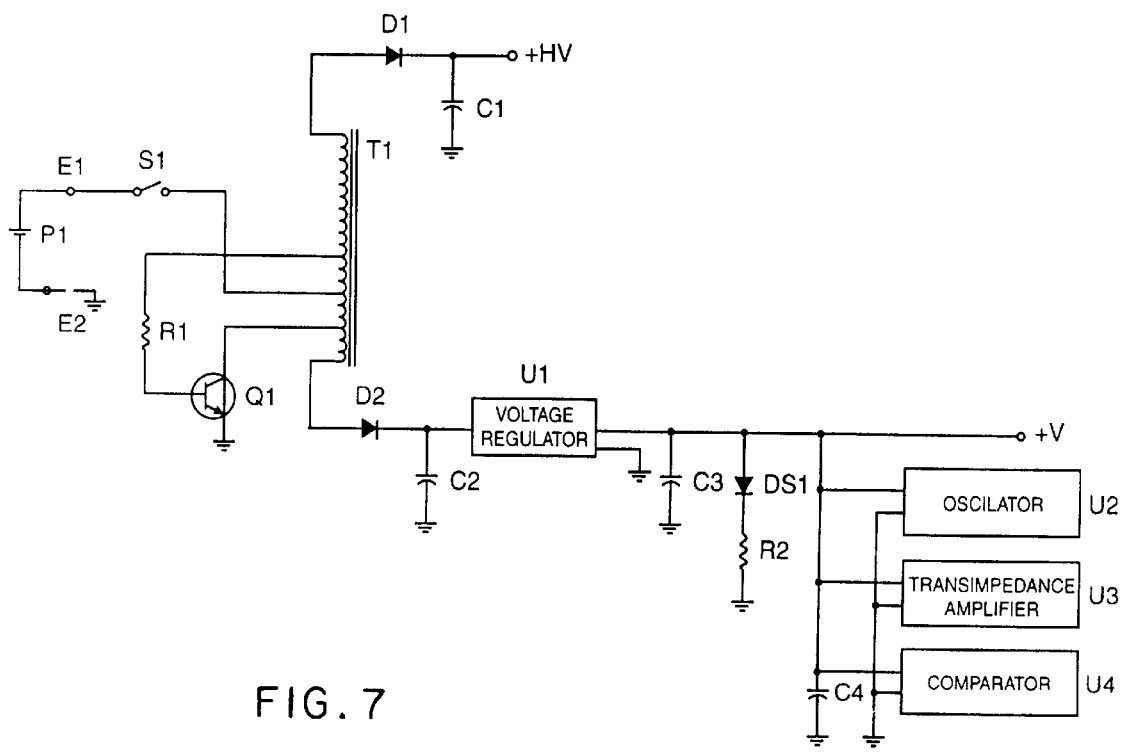
FIG. 7 is a circuit diagram of power circuitry used in the detecting apparatus of FIGS. 1–3.
Figure 8:
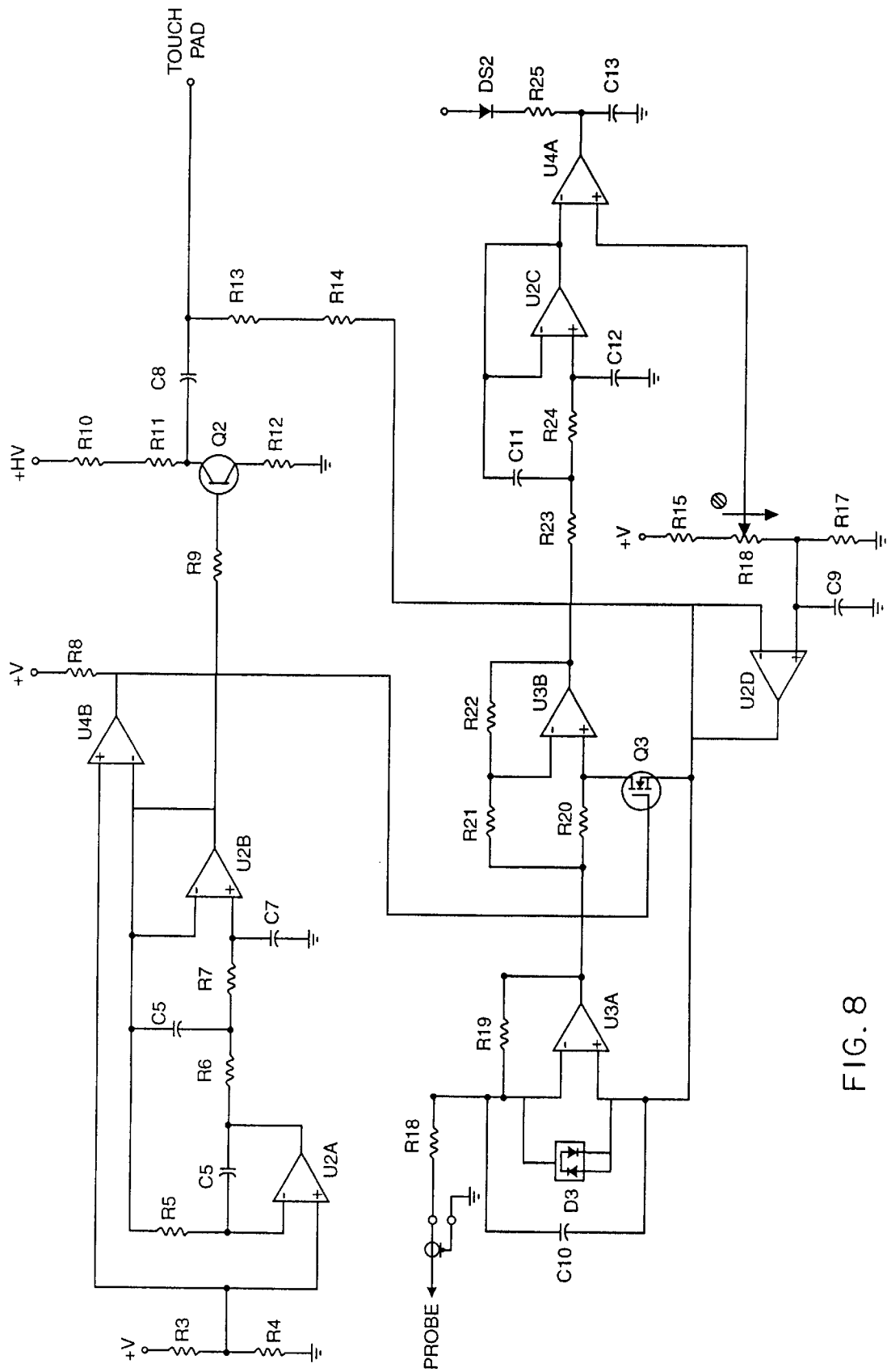
FIG. 8 is a circuit diagram of signal producing and sensing circuitry used in the detecting apparatus of FIGS. 1–3.

FIGS. 7 and 8 illustrate exemplary circuitry schematics which can be used to carry out the process described above. A power converter is illustrated in FIG. 7 and comprises a power source P1 having electrical contact points E1 and E2 and a ground. When the switch S1 turns the apparatus 10 on, power in the form of a direct voltage is sent through resistor R1, transistor Q1 and ground, and transformer T1. The battery voltage is stepped up to a higher voltage, typically up to 300 volts, by transformer T1, diode D1 and capacitor C1 and ground. The other portion of the initial voltage is regulated as it passes through diode D2, capacitor C2 and ground, voltage regulator U1 and turns on the green indicator light by passing through capacitor C3 and ground, light-emitting diode DS1 and resistor R2 and ground. The operating voltage +V is then supplied to oscillator U2, a transimpedance amplifier U3 and a comparator U4 coupled with capacitor C4 and ground for further processing.

Referring specifically now to FIG. 8, the operating voltage +V is supplied to the oscillator U2A and U2B and corresponding resistors R3–7 and capacitors C5–7 which produces a low-voltage sine wave output at approximately 28 Hz. The low-voltage sine wave output is coupled to a high-voltage amplifier Q2 and corresponding resistors R9–14 and capacitor C8, which amplifies the alternating current sine wave and couples this resulting signal to the electrode touchpad. This operator contacts the touchpad with his or her body, which becomes a source of electrical stimulus to the sample gemstone under test. A comparator U4B and associated resistor R8 senses the oscillators instantaneous voltage and generates a high or low output corresponding to the positive or negative half-cycle, respectively, at the touchpad to create a signal in phase with the transmitted sine wave signal. This output signal from the comparator U4B controls the inverting/non-inverting amplifier U3B and associated transistor Q3, and resistors R20–22.

A bias voltage is established using the supply voltage by a resistive divider comprised of resistors R15 and R17 and ground, variable resistor R18, capacitor C9 and ground, and buffer amplifier U2D. The bias voltage is typically one-half that of the supply voltage, but can be altered to raise or lower the sensitivity of the apparatus 10. The bias voltage is applied the transimpedance amplifier U3A and associated resistors R18 and R19, capacitor C10, and diode D3. Sensed signals are passed through the probe 16 and subsequently pass through the transimpedance amplifier U3A and associated components where the probe current is converted to a voltage which drives the inverting/non-inverting stage U3B, followed by the active low-pass filter U2C and associated resistors R23 and R24 and capacitors C11 and C12 and ground.

The inverting/non-inverting stage U3B and the low-pass filter U2C form a synchronous detector, the output of which remains equal to the bias voltage under no-signal conditions. The leading-phase sine wave that appears at the transimpedance amplifier U3A output due to capacitive coupling is chopped to produce a signal at the output of the inverting/non-inverting stage U3B which has equal excursions above and below the direct current bias level, the average value as seen by the low-pass filter U2C being equal to the bias voltage level. Hum and other periodic noise are filtered out by the synchronous detector as they are not coherent with the detector switching signal and have no elevated direct current component after being rectified.

On the other hand, when the probe signal is in-phase with the detector switching signal, the synchronous detector becomes essentially a full-wave rectifier, and the output of the low-pass filter U2C is a direct current voltage which is proportional to the amplitude of the in-phase signal, which is greater than the bias voltage. A threshold comparator U4A detects this increase in voltage and lights the light-emitting diode DS2 associated with resistor R25 and capacitor C13 and ground, to indicate that the sample has conducted the transmitted signal and consequently the sample gemstone is a man-made simulant.

The process and associate apparatus 10 of the present invention rejects signals with the leading phase characteristic common to noise and other non-transmitted signals, while accepting those signals with an in-phase, or the conducted transmitted signal, characteristic. This results improving the sensitivity of the apparatus 10. Due to the increase in sensitivity, not only are false positive results eliminated, but external power is not required and the apparatus 10 can be relatively small and battery powered enabling the operator to freely transport the apparatus 10 within his or her pocket.

Although a particular embodiment has been described in detail for purposes of illustration, various modifications may be made to each without departing from the scope and spirit of the invention. Accordingly, the invention is not to be limited, except as by the appended claims.

What is claimed is:

1. An apparatus for detecting man-made gemstones, comprising:

an alternating current signal generating and sensing electronic circuitry;

an electrode delivering an alternating current stimulus generated by the electronic circuitry; and a sensing probe conductively coupled to the electronic circuitry;

wherein the alternating current stimulus is transmitted to the gemstone from the stimulus electrode and upon detection of the transmitted signal by the probe an alarm is activated to indicate the presence of a man-made gemstone.

2. The apparatus of claim 1, wherein the electronic circuitry includes a filter which eliminates non-transmitted signals.

3. The apparatus of claim 1, wherein the electronic circuitry includes means for producing an alternating current sine wave.

4. The apparatus of claim 1, wherein the electronic circuitry is disposed within a hand-held housing and the signal-delivering stimulus electrode comprises a body-contact touchpad extending through the housing, wherein an operator of the apparatus contacts the touchpad and conducts the alternating current signal to the tested gemstone.

5. The apparatus of claim 4, wherein the hand-held housing includes a battery which supplies power to the electronic circuitry.

6. The apparatus of claim 1, wherein the alarm comprises a light-emitting diode.

7. An apparatus for detecting man-made gemstones, comprising:

a housing;

an alternating current sine wave signal producing and sensing electronic circuitry disposed within the housing and having a filter;

a power source for the electronic circuitry;

a signal-transmitting stimulus electrode comprising a body-contact touchpad exposed through the housing which delivers an alternating current signal produced by the electronic circuitry; and a probe conductively coupled to the electronic circuitry and extending from the housing;

wherein the alternating current is transmitted to the gemstone through an operator of the apparatus contacting the touchpad and holding a gemstone, and upon detection of the transmitted signal by the probe an alarm is activated to indicate the presence of a man-made gemstone.

8. The apparatus of claim 7, wherein the power source comprises a battery disposed within the housing.

9. The apparatus of claim 8, wherein the alarm comprises a light-emitting diode.

10. The apparatus of claim 7, wherein the sensing circuitry comprises a transimpedance amplifier, a inverting/non-inverting amplifier, and a low-pass filter.

11. The apparatus of claim 10, wherein the inverting/non-inverting amplifier and the low-pass filter comprise a synchronous detector which maintains a reference voltage under conditions where no transmitted signal is detected.

12. A process of detecting man-made gemstones, comprising the steps of:

producing an alternating current signal;

transmitting the signal to a sample gemstone;

probing the sample gemstone with a conductive probe in an attempt to sense a transmitted signal conducted through the gemstone;

determining whether any sensed signal is the transmitted signal; and activating an alarm if the transmitted signal is detected by the probe.

13. The process of claim 12, wherein the producing step includes the step of producing an alternating current sine wave signal.

14. The process of claim 12, wherein the transmitting step includes the steps of delivering the alternating current signal to a touchpad and conducting the transmitted signal through an operator of the apparatus and into the gemstone.

15. The process of claim 12, including the steps of producing a direct current bias voltage and a detector switching signal in phase with the alternating current signal.

16. The process of claim 15, wherein the determining step includes the steps of filtering non-transmitted signals from the sensed signal.

17. The process of claim 16, wherein the filtering step further includes eliminating non-transmitted signals by chopping a portion of a ninety degree shifted, capacitively coupled sensed signal.

18. The process of claim 17, wherein the filtering step further includes comparing the phase of the sensed signal with the detector switching signal, rectifying the signal, and measuring an increase in voltage over the bias voltage.

19. A process of detecting man-made gemstones, comprising the steps of:

producing an alternating current sine wave signal;

producing a direct current bias voltage and a detector switching signal in phase with the alternating current sine wave signal;

transmitting the alternating current sine wave signal to a touchpad;

transmitting the alternating current sine wave signal through an operator of the apparatus and into a sample gemstone;

probing the sample gemstone with a conductive probe in an attempt to sense a transmitted signal conducted through the gemstone;

determining whether any sensed signal is the transmitted signal by comparing the sensed signal with the detector switching signal and the bias voltage; and activating an alarm if the transmitted signal is detected by the probe.

20. The process of claim 19, wherein the determining step includes filtering non-transmitted signals from the sensed signal by eliminating non-transmitted signals by chopping a portion of a ninety degree shifted, capacitively coupled sensed signal and comparing the phase of the sensed signal with the detector switching signal, rectifying the signal, and measuring an increase in voltage over the bias voltage.

* * * * *